United States Patent
Austin et al.

(10) Patent No.: US 10,448,981 B2
(45) Date of Patent: Oct. 22, 2019

(54) FIXED BONE PLATE FOR ROTATIONAL AND TRANSLATIONAL FIRST METATARSAL OSTEOTOMY PROCEDURES

(71) Applicant: Neutin Orthopedics, LLC, Millersville, MD (US)

(72) Inventors: Albert Eugene Austin, Millersville, MD (US); Steven Keith Neufeld, Washington, DC (US); Paul Stuart Cooper, Potomac, MD (US); Kent Ellington, Charlotte, NC (US); Matthew M. Buchanan, Chattanooga, TN (US); Daniel Cuttica, Falls Church, VA (US)

(73) Assignee: Neutin Orthopedics, LLC, Millersville, MD (US)

( * ) Notice: Subject to any disclaimer, the term of this patent is extended or adjusted under 35 U.S.C. 154(b) by 428 days.

(21) Appl. No.: 14/991,890

(22) Filed: Jan. 8, 2016

(65) Prior Publication Data
US 2016/0199110 A1 Jul. 14, 2016

Related U.S. Application Data

(60) Provisional application No. 62/124,948, filed on Jan. 8, 2015.

(51) Int. Cl.
*A61B 17/80* (2006.01)
*A61B 17/56* (2006.01)

(52) U.S. Cl.
CPC ...... *A61B 17/8061* (2013.01); *A61B 17/8085* (2013.01); *A61B 2017/565* (2013.01)

(58) Field of Classification Search
CPC .. A61B 17/80; A61B 17/8061; A61B 17/8085
See application file for complete search history.

(56) References Cited

U.S. PATENT DOCUMENTS

| | | | |
|---|---|---|---|
| 5,529,075 A | 6/1996 | Clark | |
| 6,203,545 B1 | 3/2001 | Stoffella | |
| (Continued) | | | |

OTHER PUBLICATIONS

Coetzee, C. Scarf Osteotomy for Hallux Valgus Repair: The Dark Side. Foot and Ankle International Jan. 2003; 24(1): 29-33.
(Continued)

*Primary Examiner* — Christopher J Beccia
(74) *Attorney, Agent, or Firm* — Potomac Law Group, PLLC; Mark A. Catan (57) ABSTRACT

An internal fixed bone plates provided for load bearing and non-load bearing fixation for a rotational or translational osteotomy procedure for hallux valgus correction in the first metatarsal bone of the foot. The example include a set design plate having screw holes for attachment of the fixed bone plate to the first metatarsal bone of the foot. Screw holes are located on the plate, including screw holes on top or sides of the plate and screw holes at the ends of the plate. A temporary small holding wire hole may be located in the plate to hold the plate to the bone temporarily. This plate allows both angled screw fixation of various movable, rotational and translational osteotomy and locking screw hole capability to ensure stability when fixating the preferred rotational and translational osteotomy procedure.

19 Claims, 4 Drawing Sheets

(56) References Cited

U.S. PATENT DOCUMENTS

| | | | |
|---|---|---|---|
| 6,565,570 B2* | 5/2003 | Sterett | A61B 17/025 606/280 |
| 7,008,428 B2 | 3/2006 | Cachia et al. | |
| 2004/0102778 A1 | 5/2004 | Huebner et al. | |
| 2005/0065521 A1 | 3/2005 | Steger et al. | |
| 2009/0306724 A1* | 12/2009 | Leither | A61B 17/8057 606/289 |
| 2010/0256687 A1 | 10/2010 | Neufeld et al. | |
| 2014/0180343 A1* | 6/2014 | Gaudin | A61B 17/8061 606/283 |

OTHER PUBLICATIONS

Easley, ME. Current concepts review: hallux valgus part II: operative treatment. Foot and Ankle International 28(6): 748-758, 2007.
Trnka HJ, Parks BG, Ivanic G, Chu IT, Easley ME, Schon LC, Myerson MS. Six metatarsal shaft osteotomies: mechanical and immobilization comparisons. Clin. Ortho Relat. Res. 2000; 381: 256-265.
Adam, SP, Choung SC, Gu Y, O'Malley MJ, Outcomes after Scarf osteotomy for treatment of Adult hallux valgus deformity. Clin Orthop Relat Res. 2011; 469: 854-859.
Trnka, H. Hofstaetter, S Hofstaetter, J Gruber F, Adams B, Easley M. Intermediate Term Results of the Ludloff Osteotomy in One Hundred and Eleven Feet. JBJS, vol. 90-A(3), Mar. 2008, 531-539.
Thangarajah, T, Ahmed, U. The early functional outcome of Mau osteotomy for the correction of moderate-severe hallux valgus. Orthopedic Reviews Dec. 2013, vol. 5:e37.
Patton GW, Zelichowski JE. Middiaphyseal Osteotomies, Chapter 16. pp. 215-225.
Acevedo et al. "Mechanical comparison of cyclic loading in five different first metatarsal shaft osteotomies", Foot Ankle International 2002; 23(8): 711-716.
Aminian et al., "Scarf Osteotomy for Hallux Valgus Deformity: An Intermediate Followup of Clinical and Radiographic Outcomes", Foot Ankle Int. 2006; 27: 883-886.
Chang et al., "Relative Strengths of Internal Fixation in Osteotomies and Arthrodesis of the First Metatarsal", Chapter 21, pp. 119-127.
Cisar et al., "Osteotomy According to Ludloff in Hallux Valgus Surgery", Die Osteotomie nach Ludloff bei der Hallux-valgus-Operation, Aktuelle Traumatologie, 13 (1983) 247-249. English Abstract provided.
Crevoisier et al., "The Scarf Osteotomy for the Treatment of Hallux Valgus Deformity: A Review of 84 Cases", Foot/Ankle International, 22(12): 970-976, 2001.
David et al., "Retrospective Analysis of the Mau Osteotomy and Effect of a Fibular Sesamoidectomy", Journal of Foot Ankle Surgery 1998; 37: 212-216.
Glover et al., "Early Results of the Mau Osteotomy for Correction of Moderate to Severe Hallux Va lgus: A Review of 24 Cases", Journal of Foot and Ankle Surgery, 2008, 47(3); 237-242.
Hyer et al., "A Comparison of the Crescentic and Mau Osteotomies for Correction of Hallux Valgus", Journal of Foot and Ankle Surgery, Mar./Apr. 2008, vol. 47, No. 2, 103-111.
Lipscombe et al., "Scarf Osteotomy for the Correction of Hallux Valgus: Midterm Clinical Outcome", Journal of Foot Ankle Surgery, 47: 273-277, 2008.
Mau et al., "The operative treatment of hallus valgus (Follow-Up)", Die operative Behandlung des hallux valgus (Nachuntersuchungen), Dtsch Z Chir, 197:361-377, 1926, English translation attached.
Miller et al., "Inverted 2-scarf Osteotomy for Hallux Valgus Deformity Correction: Intermediate-term Results in 55 Patients", Journal of Foot and Ankle Surgery, 2011, 50; 55-61.
Neese et al., "Mau Osteotomy: An Alternative Procedure to the Closing Abductory Base Wedge Osteotomy", The Journal of Foot Surgery, 1989, pp. 352-362.
Neese et al., "The Modified Mau-Reverdin Double Osteotomy for Correction of Hallux Valgus: A Retrospective Study", Journal of Foot Ankle Surgery, 2009; 48: 22-29.
O'Briain et al., "Use of a Geometric Formula to Improve the Radiographic Correction Achieved by the Scarf Osteotomy", Foot and Ankle International Aug. 2012; 33 (8): 647-654.
Sammarco, "Surgical Strategies: Mau Osteotomy for Correction of Moderate and Severe Hallux Valgus Deformity", Foot and Ankle International Jul. 2007; 28(7): 857-864.
Saxena et al,, "The Ludloff Osteotomy: A critical Analysis", Journal of Foot and Ankle Surgery, 1997; 36:100-105; 159-160.
Steck et al., "Long Z-Osteotomy: A Review and New Modification to Correct Troughing", Journal of Foot and Ankle Surgery, 2001;vol. 40, No. 5: 305-310.
Vienne et al., "Comparative Mechanical Testing of Different Geometric Designs of Distal First Metatarsal Osteotomies", Foot/Ankle International 28:232-236, 2007.
Weil, "Scarf Osteotomy for Correction of Hallux Valgus Historical Perspective, Surgical Technique, and Results", The Hallux, vol. 5, No. 3, Sep. 2000, pp. 559-580.

\* cited by examiner

FIXED BONE PLATE FOR ROTATIONAL AND TRANSLATIONAL FIRST METATARSAL OSTEOTOMY PROCEDURES

CROSS-REFERENCE TO RELATED APPLICATIONS

The present application claims the benefit of U.S. Provisional Application No. 62/124948, filed Jan. 8, 2015, which is hereby incorporated by reference herein in its entirety.

FIELD

This present disclosure relates generally to medical devices, and, more particularly, to fixation devices for a osteotomy procedures.

BACKGROUND

In the literature, there are various described methods to obtain hallux valgus correction of the first metatarsal or bunion correction. A bunion or "hallux valgus" or "hallux abducto-valgus" are the most commonly used medical terms associated with a bunion anomaly, where "hallux" refers to the great toe, "valgus" refers to the abnormal angulation of the great toe commonly associated with bunion anomalies, and "abductus/-o" refers to the abnormal drifting or inward leaning of the great toe towards the second toe, which is also commonly associated with bunions. "Hallux abducto" refers to the motion the great toe moves away from the body's midline.

Three of many commonly performed procedures to correct bunion or a hallux valgus deformity in the foot are discussed below.

A scarf, or z-osteotomy, was described by Meyer (1926) and Burutaran (1976) and used experimentally for hallux valgus correction by Dr. Charles Gudas in 1984, who used a Z-cut osteotomy of the first metatarsal to gain correction of the metatarsus primus varus and bunion deformity. The word scarf is a term used in carpentry (an architectural term) to describe the notching or cutting of two pieces of wood so that they interlock and form a strong bond. This notching technique is the basis of the scarf osteotomy procedure. In this procedure, the long bone, or metatarsal, of the first toe is sliced horizontally and two transverse cuts or notches are made at each end of the bone. The lower piece of the first metatarsal is moved inward to reduce the angle between the first and second metatarsals and bring the toes closer together.

The scarf osteotomy is a medial, longitudinal osteotomy cut that combines two transverse cuts at each end of the longitudinal osteotomy cut. The scarf osteotomy has gained popularity in Europe in recent years because it is versatile due to its tri-planar configuration, allowing correction of the IMA (intermetatarsal angle) and DMAA (distal metatarsal articular angle) simultaneously through translation and rotation.

A scarf osteotomy surgical procedure entails making a dorsal/medial skin incision extending from the first metatarsal phalangeal joint to the base of the first metatarsal joint. Once exposure is obtained, an osteotomy is performed which cuts the metatarsal bone. There are two components to the scarf osteotomy. A longitudinal osteotomy cut is then followed by two transverse cuts. The longitudinal osteotomy cut varies from 25-40 mm long depending on the length of the metatarsal and amount of hallux valgus correction required. The transverse osteotomy cuts are made at the distal and proximal ends of the longitudinal osteotomy cut and the transverse cuts vary from 25 to 90 degrees in relation to the longitudinal osteotomy cut. There are variations on the osteotomy cut, but they essentially follow the same longitudinal osteotomy cut and 2 transverse cuts.

After removal by a medical saw blade of the medial eminence of the metatarsal head or bump on the metatarsal head, the first component of the scarf longitudinal osteotomy cut starts about 3 mm to 4 mm below the dorsal/top medial surface of the metatarsal head and approximately 5 mm proximal to the articular surface of the first metatarsal. The scarf longitudinal osteotomy cut continues down the long axis of the metatarsal bone, parallel to the proximal medial border and continuing plantarward so that it reaches the lateral surface approximately 3-5 mm dorsal of the plantar cortex, ending approximately 20 mm distal from the metatarsal-cuneiform joint articulation. The longitudinal osteotomy cut runs parallel to the plantar surface, about 3 mm to 4 mm above the plantar cortex of the metatarsal. The second component of the scarf osteotomy is the transverse osteotomy bone cuts. They are approximately made at 25-90 degree angles in relation to the longitudinal osteotomy cut, forming proximal and distal "chevron like" osteotomy cuts. The distal/dorsal transverse osteotomy cut is approximately 5 mm proximal to the margin of the dorsal cartilage and at an approximate angle of 25-90 degrees to the longitudinal osteotomy cut and is made from dorsal to plantar. The proximal/plantar transverse osteotomy cut is approximately 20 mm distal to the articular surface of the base of the metatarsal and is angled out the plantar cortex through the metatarsal bone at approximately a 45 to 60 degree angle to the longitudinal osteotomy cut and is made from plantar to dorsal.

Once the scarf osteotomy is completed, the section of the plantar metatarsal bone is gently pulled laterally and the section of the dorsal metatarsal bone is gently pulled medially to allow for appropriate hallux valgus correction of the metatarsal bone.

The scarf osteotomy is an intrinsically stable osteotomy cut but under weight or load bearing conditions may cause stress risers or fractures dorsally across the metatarsal shelf from the proximal plantar osteotomy. The scarf osteotomy also presents the possibility of "troughing" of the two halves of the metatarsal bone which happens when the cortices wedge into the softer cancellous bone of the metatarsal shaft. This causes a functional elevation or dorsiflexion of the first metatarsal that may lead to a pronated foot and lesser metatarsal bone overload.

Scarf osteotomies have been previously fixated with K-wires and screws, but most notably always 2 or 3 screws. The fixation techniques reported vary in steps, screw diameter sizes used, k-wire sizes used, placement, etc.

The Ludloff osteotomy was first described in 1918 and is a through and through osteotomy in the transverse plane extending dorsal-proximal to plantar-distal when viewed in the sagittal plane (from the side). The Ludloff osteotomy allows for intermetatarsal angle reduction, lengthening, and plantar displacement. The osteotomy is not intrinsically stable, and therefore strong fixation is necessary.

A Ludloff osteotomy surgical procedure entails making a dorsomedial incision over the first metatarsal of the foot which extends from the first metatarsal phalangeal joint distally to the base of the first metatarsal joint proximally. Once exposure is achieved, the osteotomy is performed using a standard medical surgical sawblade to cut the bone. The Ludloff osteotomy begins dorsally about 1 cm to 1.5 cm distal to the base of the first metatarsal, angled approximately 30 degrees, extending from dorsal-proximal to plantar-distal, and ends just proximal (before) to the sesamoid complex at the first metatarsal distal base. The Ludloff osteotomy cut is thorough and through for about two-thirds way through the metatarsal bone. At this point the surgeon stops the osteotomy cut and temporarily fixates the metatarsal bone at the proximal-dorsal location. This temporary fixation, before the Ludloff osteotomy is completed, allows the surgeon to rotate the metatarsal bone laterally after completing the Ludloff osteotomy cut. Temporary fixation is completed and various authors describe fixation by using kwires or screws. The Ludloff osteotomy cut is then completed and the dorsal aspect of the metatarsal bone is gently shifted laterally to obtain the desired hallux valgus correction, using the temporary fixation point located at the proximal-dorsal location as an axis point or rotation point. Lateral correction of the dorsal aspect of the metatarsal bone is performed by pulling the plantar metatarsal fragment medially and the dorsal metatarsal fragment laterally with manual pressure applied to the medial aspect of the first metatarsal head. The Ludloff osteotomy is then fixated distally with kwires or screws and the osteotomy correction is complete. Ludloff osteotomies have previously fixated with no internal fixation until reported with internal fixation of screws, kwires or a combination of screws and kwires.

The Mau osteotomy was first used in 1915 and presented by Mau in 1926. Mau modified the Ludloff osteotomy cut by changing the direction of the osteotomy cut. The ludloff osteotomy is a through-in-through, oblique diaphyseal osteotomy cut extending from dorsal proximal to plantar distal on the first metatarsal bone. Mau reversed the Ludloff cut and challenged the stability of the Ludloff osteotomy by creating a dorsal shelf to help resist weight-bearing forces. The Mau osteotomy is a through-in-through oblique diaphyseal osteotomy cut from plantar proximal to dorsal distal through the shaft of the first metatarsal.

The Mau osteotomy is made parallel to the weight bearing plane and its long dorsal shelf of bone supports the distal fragment, making dorsal displacement of the first metatarsal osteotomy cut unlikely. The Mau type osteotomy is an intrinsically stable metatarsal osteotomy cut because of the dorsal shelf that resists dorsal displacement forces. Weight bearing on the foot compresses the osteotomy.

The Mau osteotomy surgical technique is achieved with a standard medial approach incision to obtain exposure of the first metatarsal bone. After identifying the tarsometatarsal joint (TMTJ) and using a medical power saw, the oblique Mau osteotomy cut is begun about 1-2 centimeters from the first metatarsal head and made from dorsal-distal to proximal-plantar, parallel to the weight bearing surface of the first metatarsal bone. The plantar metatarsal bone fragment is then laterally rotated transversely and realigned to correct the desired anatomical alignment. Once appropriate realignment of the first metatarsal bone is completed to correct the hallux valgus deformity, various methods of fixation are inserted into the first metatarsal to hold the metatarsal in its realigned position.

Mau osteotomies have been previously fixated with K-wires and screws, but most notably always 2 or 3 screws. The fixation techniques reported vary in steps, screw diameter sizes used, k-wire sizes used, placement, etc.

SUMMARY

An internal fixed bone plate device that is specific to most all rotational and translational corrective osteotomy procedures as well as with others allows for non-load bearing or load bearing. By the present application there is provided an internal fixed osteotomy plate that allows for both rotational and translational bunion osteotomy surgical correction procedures, placement of the internal fixed plate before rotation or transition of the metatarsal, then final completion and fixation of the rotational or translational osteotomy correction.

In the examples described herein, a fixed bone plate is specifically configured for dorsal or medial implantation onto the first metatarsal bone before, during and after a rotational or translational hallux valgus osteotomy correction is completed. Fixation of the rotational or translational osteotomy is allowed with anatomically configured and designed internal fixation plate designed for non-load bearing or load bearing. The fixed osteotomy internal plate can have non locking screw fixation holes which allow concentric angulation of the non-locking screws to fixate any rotational or translational osteotomy, both temporarily and for final fixation through the plate to both fixate the osteotomy and firmly hold the rotational or translational osteotomy internal fixed plate to the metatarsal bone. The rotational or translational osteotomy internal fixed plate can also have temporary fixation holes to allow for temporary fixation of the plate to the metatarsal bone before, during or after screw fixation. The rotational or translational osteotomy internal fixed plate can also have non-locking or locking screw holes, for different diameter non-locking or locking screws, to allow for final fixation and to provide strength stability of the osteotomy correction.

An advantage of the examples shown and the described herein is that precise fixation of any rotational or translational hallux valgus correction osteotomy and both non-load bearing and load bearing are allowed. A further advantage of the examples shown and described herein is that the plate will be able to accommodate a multitude of varied metatarsal anatomy sizes and metatarsal anatomy correction angles.

Other advantages and benefits of the disclosure will become apparent upon consideration of the following written description taken together with the accompanying diagrams and figures.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

For purposes of promoting an understanding of the principles of the invention, reference will now be made to the examples illustrated in the drawings and described in the following written specification. It is understood that no limitation to the scope of the invention is thereby intended. It is further understood that the present invention includes any alterations and modifications to the illustrated examples and includes further applications of the principles of the invention as would normally occur to one skilled in the art to which this invention pertains.

FIGS. 1-5 depict an internal plate fixation device 100 for load bearing and non-load bearing fixation for rotational or translational hallux valgus osteotomy procedures for hallux valgus correction in the first metatarsal bone of the foot. The plate fixation device 100 includes a straight section 1 and legs 2A, 2B, and 2C which are anatomically bended and further bendable during implementation. The legs 2A, 2B, and 2C are sized and shaped to encompass a tubular bone defining a cylindrical undersurface. The thickness of the plate decreases in the transfer from straight section to the leg 2A, 2B, 2C. The middle section 1 is straight and provides screw holes 5 for non-locking or locking screws. Each leg 2A, 2B, 2C of the plate provides a screw hole 5 for non-locking or locking screws. In embodiments, the screw holes at the ends of each leg are for locking screws. One or more screws may be provided in the middle section for non-locking screws for compression and to permit the screws to be angled to provide flexibility for the surgeon in fastening the parts of the osteotomy and the plate together.

The fixation device shown and described provides load bearing and non-load bearing fixation of the metatarsal correction for a rotational or translational osteotomy correction procedure for hallux valgus correction in the first metatarsal bone in the foot. In the example shown and described, the plate includes three top or dorsal or medial screw hole 5 locations allowing for engagement, angled screw location fixation, to allow for correction fixation once the rotational or translational hallux valgus osteotomy correction is completed of the first metatarsal bone. The three top, dorsal or medial screw hole 5 locations allow for up to 25 degree concentric angulation and oblique angulation of the screws to ensure screw engagement and fixation of the rotational or translational hallux valgus correction osteotomy across the osteotomy site, while maintaining the screws are even or flush to the plate surface. The three top, dorsal or medial screw hole 5 locations allow for fixation of the rotational or translational hallux valgus correction osteotomy once it is completed.

Proximal screw hole 5 locations at the leg 2A, 2B, 2C of the plate will be for fixation into the plate through the metatarsal bone before or after fixation of the rotational or translational hallux valgus correction osteotomy and distal screw hole 5 locations at the leg 2A, 2B, 2C end of the plate will be for fixation and locking into the plate through the metatarsal bone before or after fixation of the rotational or translational osteotomy.

In the example shown and described, the fixation device can be altered to adjust to varied anatomy by forcing or bending the proximal and/or distal edges down to the anatomy after fixation of the top or dorsal screws that are located in the plate. Various bending locations or zones are apparent on the example shown which may be utilized before, during or after application of the example shown.

Figure 1:
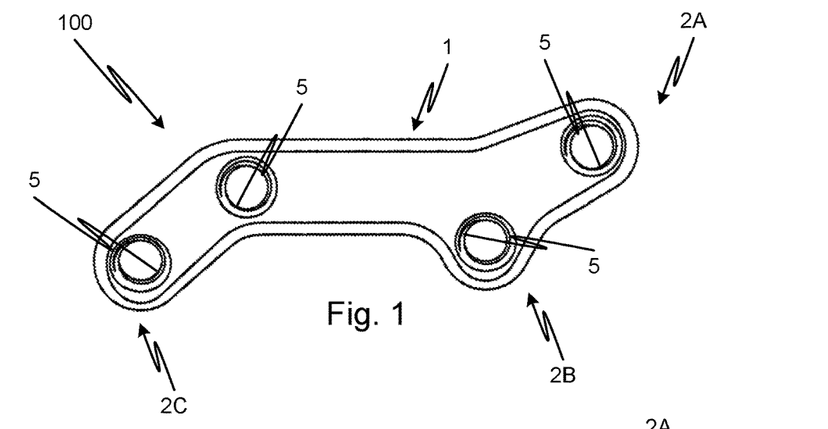
FIG. 1 is a top plain view of one example of a plate fixation device according to the present disclosure.
Figure 2:
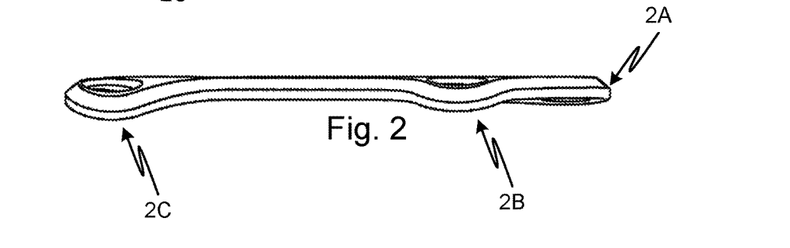
FIG. 2 is a side view of the example shown in FIG. 1.
Figure 3:
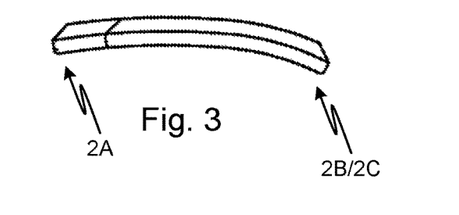
FIG. 3 is a front view of the example shown in FIG. 1.
Figure 4:
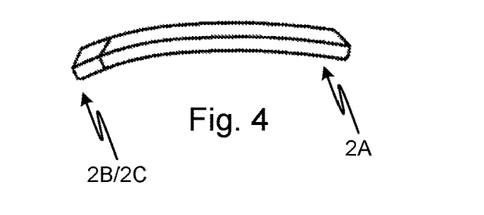
FIG. 4 is a rear view of the example shown in FIG. 1.
Figure 5:
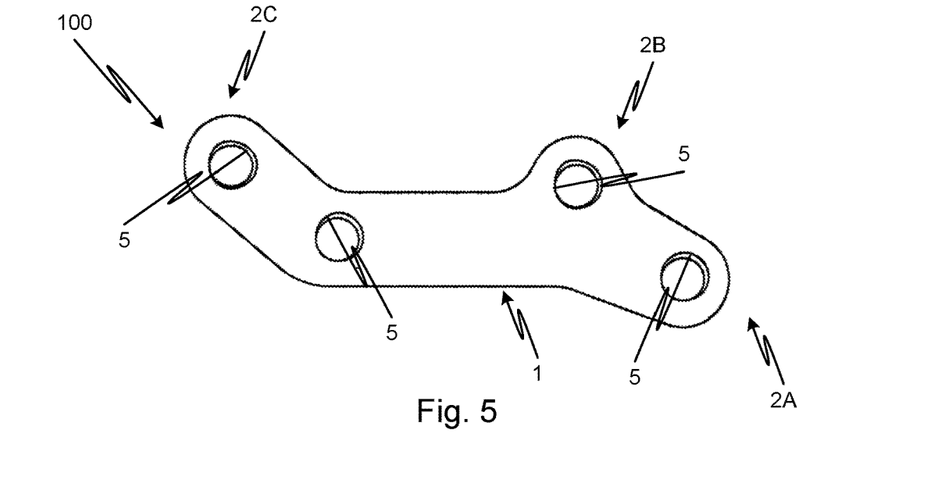
FIG. 5 is a bottom view of the example shown in FIG. 1.
Figure 6:
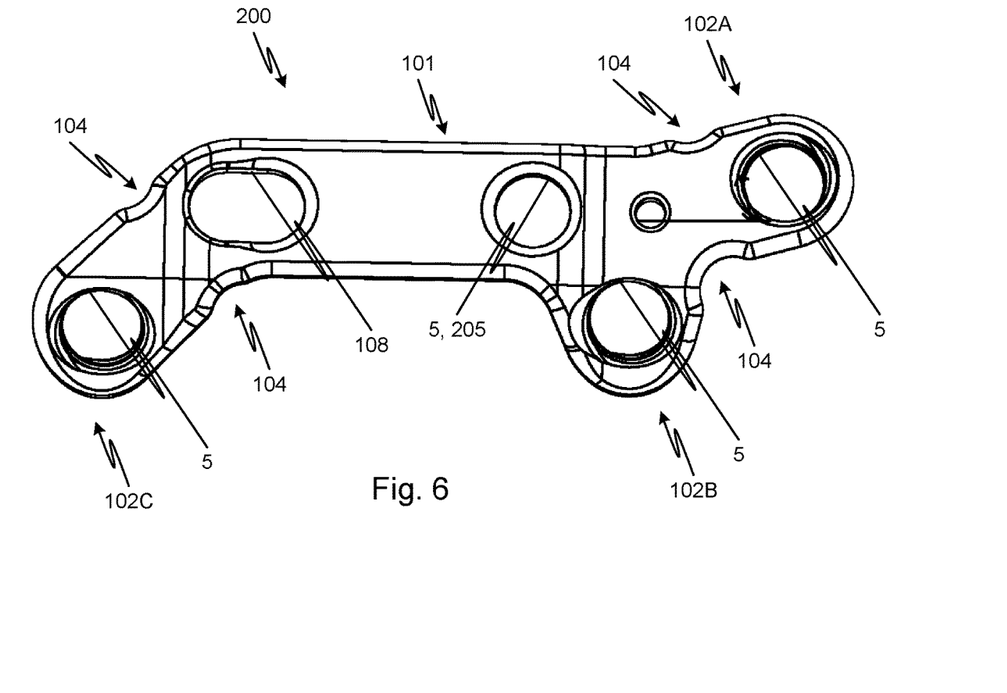
FIG. 6 Top plain view of one example of a plate fixation device according to another embodiment of the disclosed subject matter.
Figure 7:
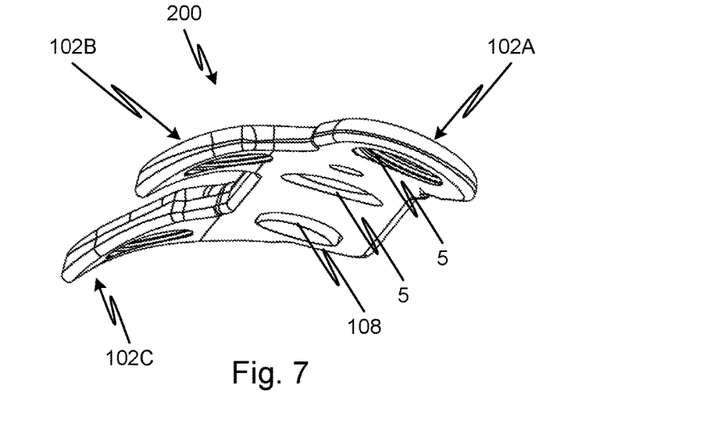
FIG. 7 is an end oblique view of the embodiment of FIG. 6 showing the cylindrical surface that is laid against the bone.

Referring now to FIGS. 6 and 7, another internal plate fixation device 200 for load bearing and non-load bearing fixation for rotational or translational hallux valgus osteotomy procedures for hallux valgus correction in the first metatarsal bone of the foot. The plate fixation device 200 includes a straight section 101 and legs 102A, 102B, and 102C. The straight, dorsal or medial section 101 provides screw holes 5 for non-locking or locking screws. Each leg 102A, 102B, 102C of the plate provides a screw hole 5 for non-locking or locking screws. The thickness of the plate decreases in the transfer from straight section to the leg 102A, 102B, 102C. One or more of the holes may be formed as indicated at 108 with an elongate shape so as to permit the positioning of a screw in hole 108 with some accommodation thereafter as other screws are affixed to the bone. The legs or bent sections 102 may have, at the points at which they join the middle section 101, a waist 104 which permit easer bending and because the waist 104 provides a predictable yield point for bending. The waist 104 also may have only a 5-20% depth of the legs or bent sections 102 so that a force applied distally can still curve the legs or bent sections 102. If the waist is too narrow, the legs or bent sections 102 would yield only at the waist 104 when a bending force is applied making it hard to customize the fit by the surgeon.

As in the embodiment 100, the fixation device 200 provides load bearing and non-load bearing fixation of the metatarsal correction for a rotational or translational osteotomy correction procedure for hallux valgus correction in the first metatarsal bone in the foot. In the example shown and described, the plate includes three top or dorsal or medial screw hole 5 locations allowing for engagement, angled screw location fixation, to allow for correction fixation once the rotational or translational hallux valgus osteotomy correction is completed of the first metatarsal bone. The three top, dorsal or medial screw hole 5 locations allow for up to 25 degree concentric angulation and oblique angulation of the screws to ensure screw engagement and fixation of the rotational or translational hallux valgus correction osteotomy across the osteotomy site, while maintaining the screws are even or flush to the plate surface. The three top, dorsal or medial screw hole 5 locations allow for fixation of the rotational or translational hallux valgus correction osteotomy once it is completed.

In the examples shown and described, the fixation device can be altered to adjust to varied anatomy by forcing or bending the proximal and/or distal edges down to the anatomy after fixation of the top or dorsal screws that are located in the plate. Various bending locations or zones are apparent on the example shown which may be utilized before, during or after application of the example shown.

Figure 8:
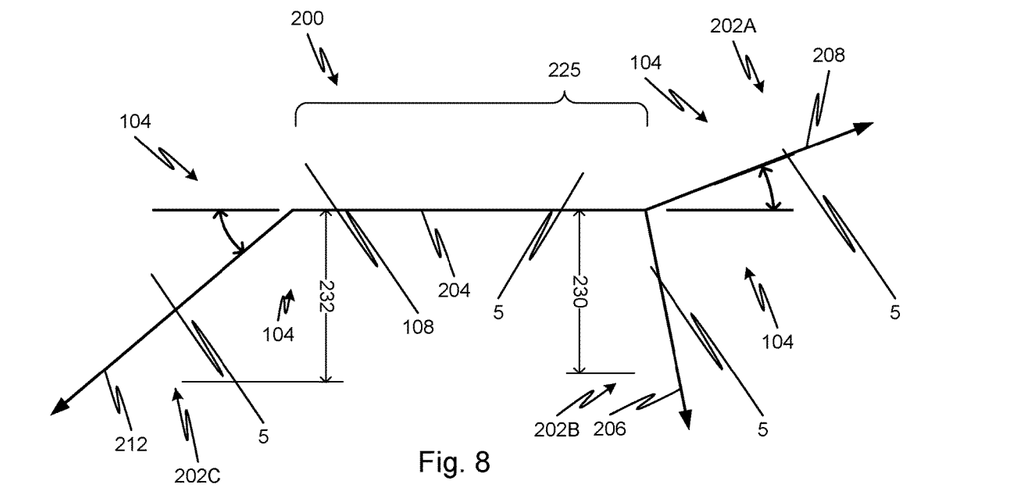
FIG. 8 is a top plan view of the plate fixation device of claim 6 showing superimposed thereon axes for measuring the angles of the legs relative to the longitudinal axis of the middle section.
Figure 9:
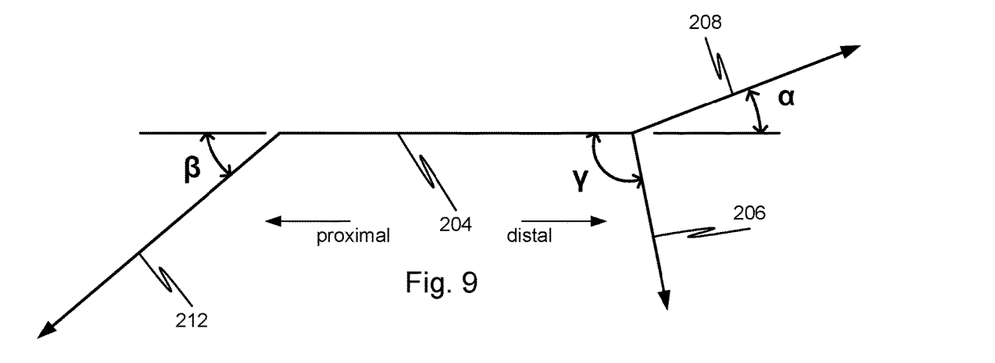
FIG. 9 defines the angles defined between selected axes identified in FIG. 8.
Figure 11:
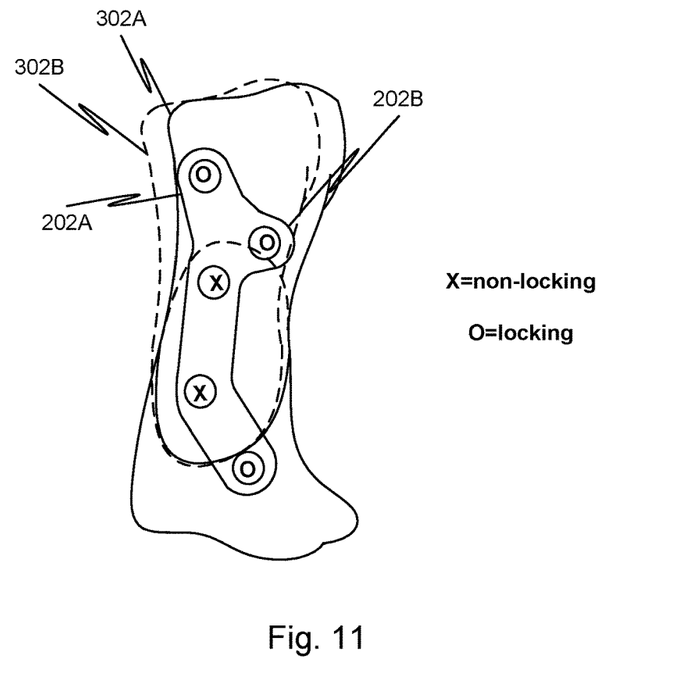
FIGS. 11 and 12 are for discussion of the features of the foregoing fixation device in exemplary contexts of Ludloff (FIG. 11 where a diagonal slice is made) and scarf (FIG. 12) osteotomy procedures.
Figure 12:
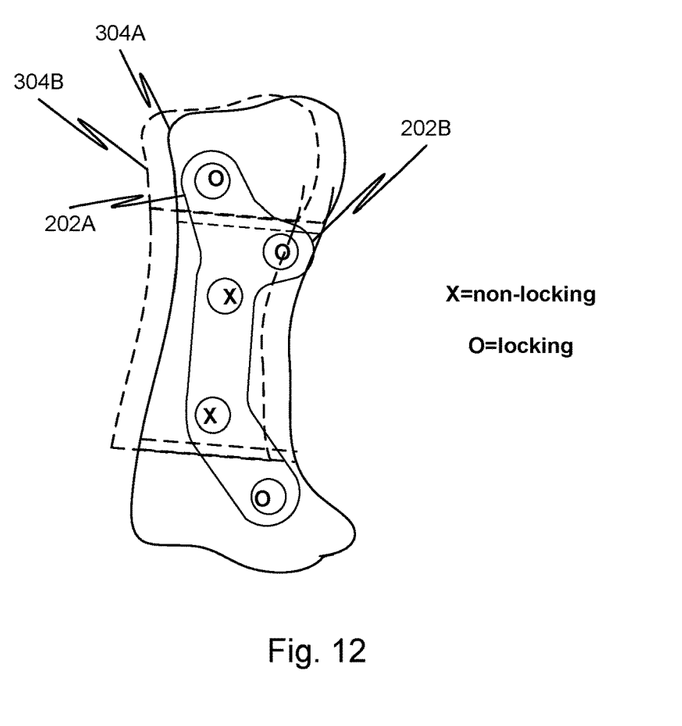

Referring to FIGS. 8 and 9, various dimensional features of the plate 200 may be seen. FIG. 9 copies the rays 208, 206, 212 and axis 204 from FIG. 8 and annotates the angles formed. Among the features, the leg 102B is shorter than leg 202C in terms of its length from a point where it stems from the middle section 225 but also in terms of its extent from the edge of the middle section in a direction perpendicular to the longitudinal axis 204 of the middle section 225. That is, dimension 230 is smaller than 232. Referring also to FIGS. 11 and 12, this shorter leg allows the leg 202B to more securely purchase (and a screw through the hole 5 in leg 202B to more securely fasten to) a distal bone portion 302B, 304B divided by osteotomy from a proximal portion and translated or rotated medially from its original position or orientation 302A, 304A. Also, the angle α is such that the hole 5 in leg 208A to more securely purchase (and a screw through the hole 5 in leg 202A to more securely fasten to) a distal bone portion 302B, 304B divided by osteotomy from a proximal portion and translated or rotated medially from its original position or orientation 302A, 304A. Also, the shorter leg 202B (compared to leg 202C) maintains the proximity of the leg 202B to the bone when the distal part 302A of the osteotomy is shifted or pivoted medially.

Figure 10:
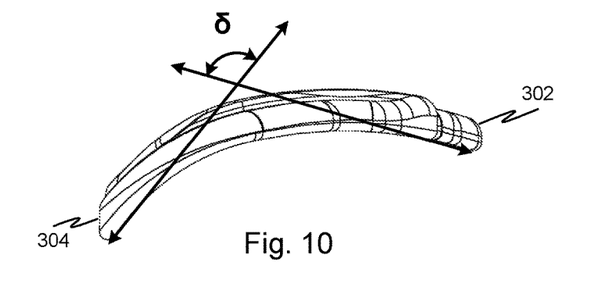
FIG. 10 shows an end view of the embodiment of FIG. 6 showing the fraction of a cylinder subtended by the curved surface of the plate.

The presence of two legs 202A and 202B with screw holes 5 at the distal end of the plate 200 provides a stronger transmission of forces into the plate 200 than a single point of attachment to the plate 200. In embodiments, the angle β is 40 degrees. In embodiments, the angle α is 20 degrees. In embodiments, the angle γ is 10 degrees. Another feature of the plate is the rotational span of the cylindrical surface indicated as δ in FIG. 10. This is a smaller span than prior art plates which makes emplacement more flexible along with the bendability of the legs 202A, 202B, and 202C.

In embodiments, the holes in the middle section indicated at 108 and 205 are formed for non-locking screws. As such they may lack threads so that screws can be angled with respect to the plate to optimize the position of the plate relative to the bone. In embodiments the elongate hold 108 has a ramp in a plane parallel to that of the drawing page such that as a screw is tightened, a drawing force is applied to the plate relative to the bone.

The fixation devices can accommodate various size diameter size locking or non-locking screws, that thread into and lock in the plate or that fixate to the plate but do not thread and lock into the plate.

The fixation devices can withstand the weight bearing capacity of the normal human being and the weight bearing load displaced to the human metatarsal bone when undergoing the normal walking gait cycle thus making it an option to bear weight immediately after fixation of the plate is applied to the rotational or translational hallux valgus correction osteotomy eliminating the concern of stress risers or fractures of the bone dorsally and troughing of the metatarsal whereby the metatarsal cortical bone collapses into the cancellous, softer bone of the metatarsal.

The fixed plate for rotational or translational osteotomy procedures has a varied thickness. Both low profile not to disrupt soft tissue and less than 1.8 mm. Thickness will be slightly thicker dorsally across the osteotomy site to provide strength across the osteotomy site and thinner at both proximal and distal ends to allow for bending of the plate and allow for low profile fixation of the plate to the metatarsal bone.

In the example shown, the fixation devices are anatomically designed to the first metatarsal bone and designed to allow completion of any rotational or translational hallux valgus correction osteotomy and fixation of any rotational or translational osteotomy while in position on the metatarsal bone.

The fixed plates for rotational or translational osteotomy procedures can be provided in a variety of lengths to accommodate a variety of first metatarsal anatomies.

The plates can be made of titanium, titanium alloy, stainless steel, plastic, thermoplastic, PEEK or PEKK like medical grade polymers, resorbable material, any metal alloy or other suitable material. In the preferred example, the straight section of the plate has a thickness of no more than 2.2 millimeters and the bent portion of the plate has a thickness of no less than 0.8 millimeters.

According to first embodiments, the disclosed subject matter includes a fixed bone plate, comprises a plate having a straight, middle section. The straight, middle section can transition to opposed anatomically curved legs. The legs can taper progressively from a first thickness in the middle section to a second thickness in the legs such that the legs may be bent during attachment to fit the anatomy of the patient, and particularly to permit conforming attachment to tubular bone. The middle section and the legs can each have at least one screw hole for non-locking or locking screws.

Variations of the first embodiments may be provided to form additional first embodiments in which the screw holes are non-threaded. Variations of the first embodiments may be provided to form additional first embodiments in which the number of said legs at one end of the middle section is two and the number of said legs at the other end is one. Variations of the first embodiments may be provided to form additional first embodiments in which the one leg of the other end is longer than a longer one of the two legs of the one end. Variations of the first embodiments may be provided to form additional first embodiments in which one of the two legs of the one end is longer than the other. Variations of the first embodiments may be provided to form additional first embodiments in which the total number of legs is three, a longest one of the two legs of the one end forming an angle with respect to a longitudinal axis of the middle section that is less than the angle formed the by the one leg of other end. Variations of the first embodiments may be provided to form additional first embodiments in which one of the screw holes is in the middle section at a point where the one leg of the other end stems from the middle section. Variations of the first embodiments may be provided to form additional first embodiments in which a section of the plate taken perpendicular to the middle section longitudinal axis has a curved shape.

According to second embodiments, the disclosed subject matter includes a method of using a plate of any of the foregoing first embodiments. The method can include performing a surgical procedure for rotational and translational uniplanar, bi-planar and multi-planar osteotomy correction by surgically affixing the fixed bone plate to a first metatarsal bone of a patient's foot.

Variations of the second embodiments may be provided to form additional second embodiments in which the method further comprises instructing the patient to walk on the foot to which the bone plate was affixed within a week of surgery. Variations of the second embodiments may be provided to form additional second embodiments in which the method further comprises and provides written instructions to the instructing that include having the patient walk on the foot to which the bone plate was affixed within a week of surgery. Variations of the second embodiments may be provided to form additional second embodiments in which the method further comprises instructing the patient to walk on the foot to which the bone plate was affixed within 48 hours of surgery. Variations of the second embodiments may be provided to form additional second embodiments in which the method further comprises and provides written instructions to the instructing that include having the patient walk on the foot to which the bone plate was affixed within 48 hours of surgery. Variations of the second embodiments may be provided to form additional second embodiments in which the method further comprises diagnosing a condition where a hallux valgus correction is indicated and performing the surgical procedure responsively to a result of the diagnosing.

According to third embodiments, the disclosed subject matter includes a fixed bone plate for attachment to the first metatarsal bone of a human being, the plate comprising a straight, middle section. The straight, middle section can transition to first and second opposed anatomically curved legs at one end of the straight middle section and a third anatomically curved leg at an opposite end of the straight middle section. Each first, second, and third leg can have at least a major portion thereof that is thinner than a thickness in the straight middle section. The middle section can have a longitudinal axis, the first, second, and third second legs forming respective first, second, and third angles with said middle section longitudinal axis. The first, second, and third second legs can have first, second, and third lengths. The first angle can be smaller than the second or third angles. The third length can be longer than either of the first or second lengths. Each of said legs can have a screw hole at an end thereof.

Variations of the third embodiments may be provided to form additional third embodiments in which the third angle is 40 degrees. Variations of the third embodiments may be provided to form additional third embodiments in which the first angle is 20 degrees. Variations of the third embodiments may be provided to form additional third embodiments in which the second length is shorter than the first or second lengths. Variations of the third embodiments may be provided to form additional third embodiments in which the middle section has an elongate screw hole at said middle section opposite end.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, fixed bone plate for rotational and translational first metatarsal osteotomy procedures. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicant intends to embrace all such alternatives, modifications, equivalents, and variations that are within the spirit and scope of the present invention

The invention claimed is:

1. A fixed bone plate for attachment to a bone in a human foot, the fixed bone plate comprising:
a plate having a straight middle section extending along a longitudinal axis and having a first thickness measured in a direction perpendicular to the bone and having a first end and a second end;
two opposed anatomically curved legs immediately adjacent to the first end of the middle section; and
one anatomically curved leg immediately adjacent to the second end of the middle section and extending away from the second end at an angle away from the longitudinal axis, wherein
all of the legs have a thickness that tapers progressively from the first thickness in the middle section to a second thickness smaller than the first thickness such that the legs may be bent during attachment to permit conforming attachment to the bone in the human foot,
the middle section and the legs each have at least one screw hole for non-locking or locking screws,
the one anatomically curved leg extending from the second end is longer than a longer one of the two opposed anatomically curved legs immediately adjacent to the first end, and
a total number of legs is three, a longest one of the two legs of the first end forming an angle with respect to the longitudinal axis of the middle section that is less than the angle formed the by the one leg of the second end.

2. The plate of claim 1, wherein the screw holes are non-threaded.

3. The plate of claim 1, wherein one of the two legs of the first end is longer than the other leg of the first end.

4. The plate of claim 1, wherein one of the screw holes is in the middle section at a point where the one leg of the second end stems from the middle section.

5. The plate of claim 1, wherein a section of the plate taken perpendicular to the middle section longitudinal axis has a curved shape.

6. A fixed bone plate for attachment to a first metatarsal bone of a human being, the plate comprising:
a plate having a straight, middle section extending along a longitudinal axis to first and second opposed ends, with first and second anatomically curved legs immediately adjacent to the first end of the straight middle section and a third anatomically curved leg with a curvature matching the first metatarsal bone immediately adjacent to the second end of the straight middle section;
each first, second, and third leg having at least a major portion thereof that is thinner as measured perpendicular to the first metatarsal bone than a thickness in the straight middle section;
the first, second, and third legs forming respective first, second, and third angles relative to the longitudinal axis of the middle section;
the first, second, and third legs having first, second, and third lengths;
the first angle being smaller than the second or third angles;
the third length being longer than either of the first or second lengths; and
each of said legs having a screw hole at an end thereof.

7. The plate of claim 6, wherein the third angle is 40 degrees.

8. The plate of claim 6, wherein the first angle is 20 degrees.

9. The plate of claim 6, wherein the second length is shorter than the first or third lengths.

10. The plate of claim 6, wherein the middle section has an elongate screw hole at said middle section opposite end.

11. The fixed bone plate according to claim 1, wherein the bone in the human foot is a first metatarsal.

12. The fixed bone plate according to claim 11, further comprising:

a waist between the middle section and at least one of the legs, wherein said at least one of the legs has a first width measured in a direction perpendicular to the thickness, and said waist has depth of 5% to 20% of the first width.

13. The fixed bone plate according to claim 6, further comprising:

a recess between the middle section and at least one of the legs, wherein said at least one of the legs has a first width measured in a direction perpendicular to the thickness, and said recess has depth of 5% to 20% of the first width.

14. The fixed bone plate according to claim 1, wherein the fixed bone plate has exactly four screw holes.

15. The fixed bone plate according to claim 6, wherein the fixed bone plate has exactly four screw holes.

16. The fixed bone plate according to claim 1, wherein the fixed bone plate has exactly five screw holes.

17. The fixed bone plate according to claim 16, wherein one of the screw holes is located in each of the legs and two screw holes are located in the middle section.

18. The fixed bone plate according to claim 17, wherein one of the screw holes in the middle section includes an oval shaped opening.

19. The fixed bone plate according to claim 6, wherein the middle section includes two screw holes, and one of the two screw holes has an oval shaped opening.

\* \* \* \* \*